United States Patent
Jian et al.

(10) Patent No.: US 6,912,915 B2
(45) Date of Patent: Jul. 5, 2005

(54) APPARATUS FOR SHEAR TESTING BONDS ON SILICON SUBSTRATE

(75) Inventors: Yue-Ying Jian, Nantou (TW); Wen-Sheng Wu, Hsinchu (TW); Jien-Ren Chen, Miaoli (TW); Wei-Jen Huang, Taoyuan (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 6 days.

(21) Appl. No.: 10/717,511

(22) Filed: Nov. 21, 2003

(65) Prior Publication Data
US 2005/0109117 A1 May 26, 2005

(51) Int. Cl.⁷ .............................................. G01N 3/08
(52) U.S. Cl. ........................................................ 73/827
(58) Field of Search .......................... 73/850, 826, 827, 73/831, 832, 842, 838, 841, 159, 866.5

(56) References Cited

U.S. PATENT DOCUMENTS

| | | | | |
|---|---|---|---|---|
| 4,750,141 A | * | 6/1988 | Judell et al. ................... | 702/95 |
| 5,641,913 A | * | 6/1997 | Watanabe ...................... | 73/827 |
| 5,969,262 A | * | 10/1999 | Ino et al. ...................... | 73/827 |
| 6,341,530 B1 | | 1/2002 | Sykes | |

* cited by examiner

*Primary Examiner*—Max Noori
*Assistant Examiner*—Corey D. Mack
(74) *Attorney, Agent, or Firm*—Birch, Stewart, Kolasch & Birch, LLP

(57) ABSTRACT

An apparatus for shear testing bonds on 8" and 12" silicon substrates. The apparatus includes a removable platform for securing the 8" wafer and a vacuum chuck for securing a 12" wafer and the removable platform at the same time. A control module controls a moving mechanism to shift a probe to contact the solder ball of the 12" substrate secured on the vacuum chuck or the solder ball of the 8" wafer on the removable platform when the removable platform is fixed on the vacuum chuck. The moving mechanism moves the probe in a direction to separate the solder ball from the wafer. A sensor measures the pulling force exerted on the probe when the probe is moved in a direction and separates the solder ball from the wafer.

20 Claims, 6 Drawing Sheets

APPARATUS FOR SHEAR TESTING BONDS ON SILICON SUBSTRATE

BACKGROUND OF THE INVENTION

1. Field of the Invention

The present invention relates to a shear testing apparatus, and in particular to a shear testing apparatus with a removable platform to accommodate different sized silicon substrates.

2. Description of the Related Art

Currently, in order to remain competitive in the IC industry, IC process engineers continuously strive to reduce the overall size and corresponding cost of IC devices. As a result of this trend toward smaller overall size, sizes of individual features of the IC device and package have decreased and circuit density has correspondingly increased. Many IC engineers pursue ways to significantly increase the feature density to take full advantage of significant decreases in feature size and thereby reduce the overall size of the IC package. Additionally, to take full advantage of significantly increased feature density, IC engineers attempt to increase the I/O pin density of IC packages. With these goals in mind, IC chip engineers have developed a wide variety of package designs to maximize I/O pin density and reduce overall package size.

One example of a package design that has a relatively high I/O density is the flip chip type package. The typical flip chip package includes an array of pads to provide interconnections between the IC devices within the die and other electrical components or IC devices external to the die. An array configuration allows the engineer to utilize the package area for I/O pad placement, as opposed to other package designs, such as surface mount packages, which typically provide I/O pins only around the package periphery.

Another example of a package design with a relatively high I/O density is the chip scale package (CSP). The typical CSP has overall package dimensions substantially equal to that of the active silicon device or die that is enclosed within the package. One such type of CSP is manufactured in wafer form and is referred to as a wafer level CSP or WLCSP. A surface mount die is a WLCSP in which I/O contacts are in bump form and located on the active side of the die.

FIG. 1A shows a die 10 of a conventional flip chip typically including a plurality of fabricated IC device structures (not shown). These IC device structures may include, for example, transistors and interconnect layers. The top surface 11 of the die has a plurality of under bump pads (not shown) formed thereon. Contact bumps 12 are formed on the under bump pads of the topmost surface 11 to provide both mechanical and electrical connections. The bottom surface of the wafer is conventionally left bare, or exposed. That is, the bottom surface is typically bare silicon.

FIG. 1B shows an enlarged cross section of a contact bump of a WLCSP die. In FIG. 1B, the conductive pad 13 is patterned over the active top surface of the die 10 and electrically connected to conventionally fabricated IC device structures (not shown). A passivation layer 14 is formed on the WLCSP die 10, covering the top surface thereof except for the conductive pad 13, to protect the IC devices therein. The under bump pad 15 is formed over portions of the passivation layer 14 and the conductive pad 13. The contact bump 12 is then grown onto the under bump pad 15.

In the conventional semiconductor process, the contact bump 12 is applied to the silicon substrate by re-flowing processes to form a semi-circular bump. It is necessary to test the mechanical strength of the intermetallic bond between the gold or solder deposit and the substrate in order to determine that the bonding method is adequate, and that the bond strength is sufficient. Difficulties arise because of the very small dimensions of the components, the precision with which the testing device must be positioned, and the very small forces and deflections which are to be measured.

In FIG. 2, the conventional test method applies a precision, thin and flat shear tool, or a probe 22, to test the adhesion between deposits and the substrate, before the dies are separated from the wafer 1 in a dicing or singulation procedure. First, the wafer 1 is fixed on a stage 21 of the test apparatus. The probe 22 is moved by some mechanical means to a start point. In order to avoid friction caused by the tool rubbing on the surface of the substrate, it is necessary for the probe 22 to be just above the substrate surface. The height of the probe 22 must be closely controlled to provide accurate force measurement, typically within +−1 μm. The probe 22 typically makes an initial point contact with the contact bump 12 on the wafer 1. The probe 22 is moved along the direction of arrow (a) and applied to the side of the contact bump 12 and moved in the direction of arrow (a) to test the mechanical strength of the bond between the contact bump 12 and the substrate. Eventually, the contact bump 12 will break, and the magnitude of the force to shear the contact bump 12 from the substrate is determined by conventional strain gauge techniques.

Furthermore, in U.S. Pat. No. 6,341,530, Sykes teaches a modified probe described for testing the force to shear a deposit of solder or gold from a substrate. These deposits have a diameter in the range 50–100 μm and serve as bonds for electrical conductors. A shear tool has a semi-cylindrical cavity which closely approximates the mean diameter of a range of substrates. This tool is adapted to re-shape substrates for a better fit. Re-shaping occurs over 30% or less of the circumference of a deposit, and to a depth of 10% or less of the diameter of the substrate.

The conventional shear test is carried out on a whole wafer. As a result, the stage and the means of moving the conventional shear test apparatus must be re-designed for each different wafer size, such as 6", 8" and 12" wafers, and semiconductor factories must prepare different shear test apparatuses for different sizes of wafers, thus increasing the cost of the apparatus. Hence, there is a need for a better shear testing method and apparatus which overcomes the aforementioned problems.

SUMMARY OF THE INVENTION

Accordingly, an object of the invention is to provide an apparatus for shear testing bonds on a semiconductor substrate.

Another object of the invention is to provide a shear testing apparatus with a removable platform to accommodate different sized substrates, such as 8" and 12" silicon wafers, and eliminate the need for additional shear testing apparatuses.

The present invention provides an apparatus for shear testing bonds on 8" and 12" silicon substrates. The apparatus includes a removable platform for securing the 8" wafer and a vacuum chuck for securing a 12" wafer or the removable platform. A control module controls a moving mechanism to shift a probe to contact the solder ball of the 12" wafer secured on the vacuum chuck or the solder ball of the 8" wafer on the removable platform when the removable platform is fixed on the vacuum chuck. The moving mechanism moves the probe in a direction to separate the solder ball from the wafer. A sensor measures the pulling force exerted on the probe when the probe is moved in a direction and separates the solder ball from the wafer.

In a preferred embodiment, the shear testing apparatus further has a heating means to heat the probe to a required temperature.

Moreover, the vacuum chuck has a plurality of aligning holes. The removable platform has a plurality of aligning pins, which are inserted in the aligning holes to position the removable platform on the vacuum chuck.

Moreover, the removable platform has a plurality of first pins to position the 8" wafer. The vacuum chuck has a plurality of second pins to position the 12" wafer or the removable platform.

In a preferred embodiment, the shear testing apparatus further has a vacuum pump. The vacuum chuck has a plurality of annularly arranged recesses and gas-exhausting holes communicated with the vacuum pump, forming a vacuum therein to secure the 12" wafer or the removable platform. The removable platform includes a base part and a moving part pivoted thereon. The moving part has a central recess and a central hole. When the removable platform is positioned on the vacuum chuck, the central recess and the central hole are communicated with the vacuum pump through the annularly arranged recesses and the gas-exhausting holes of the vacuum chuck, forming a vacuum therein to secure the 8" wafer.

Moreover, the base part of the removable platform has a locking recess and a passage communicated with the vacuum pump to fix the position of the moving part.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1A:
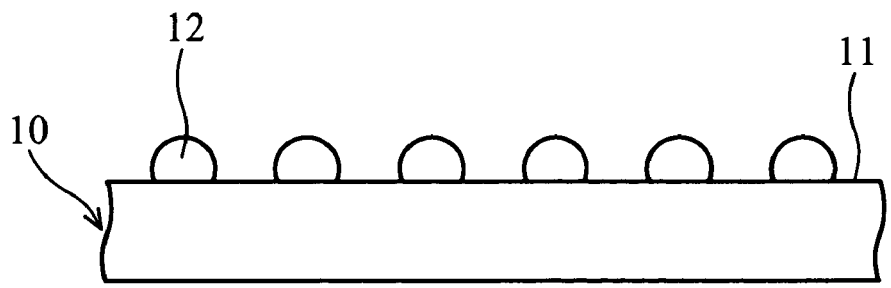
FIG. 1A is a schematic side view of a conventional WLCSP die.
Figure 1B:
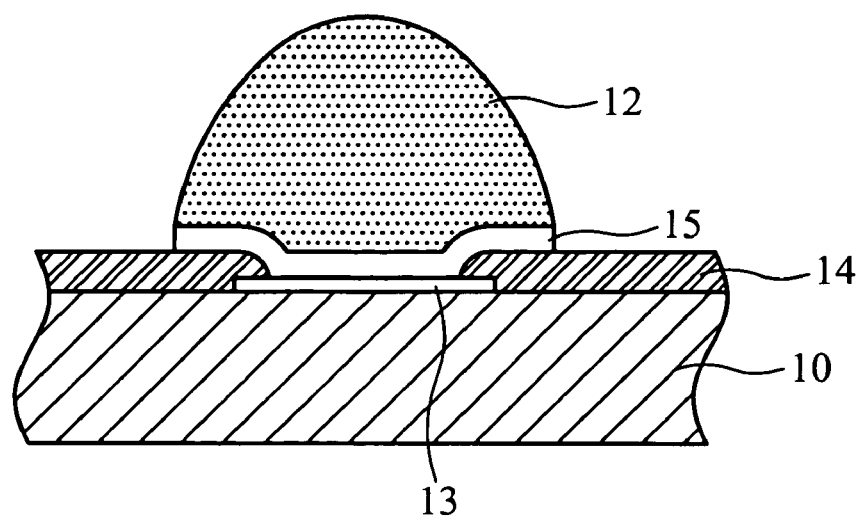
FIG. 1B is an enlarged cross section of a solder ball of a WLCSP die.
Figure 2:
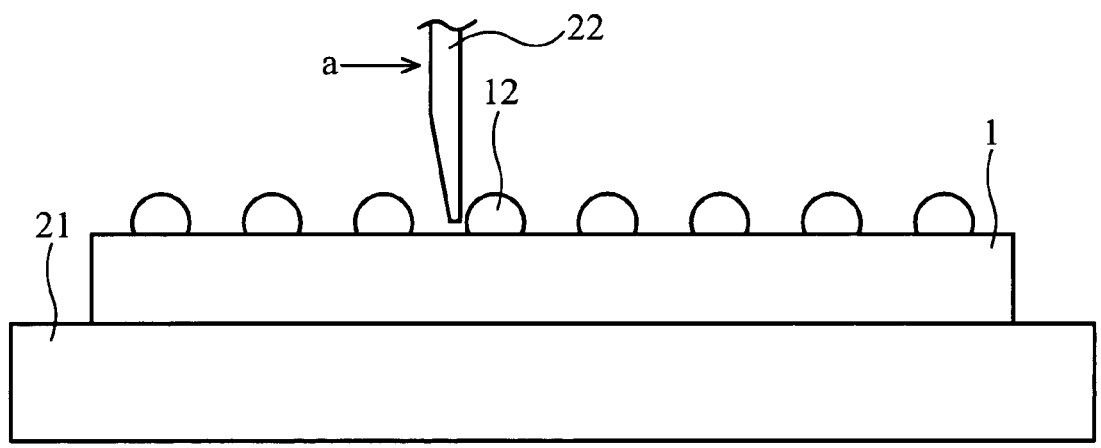
FIG. 2 is a schematic view of a conventional shear testing apparatus.
Figure 3:
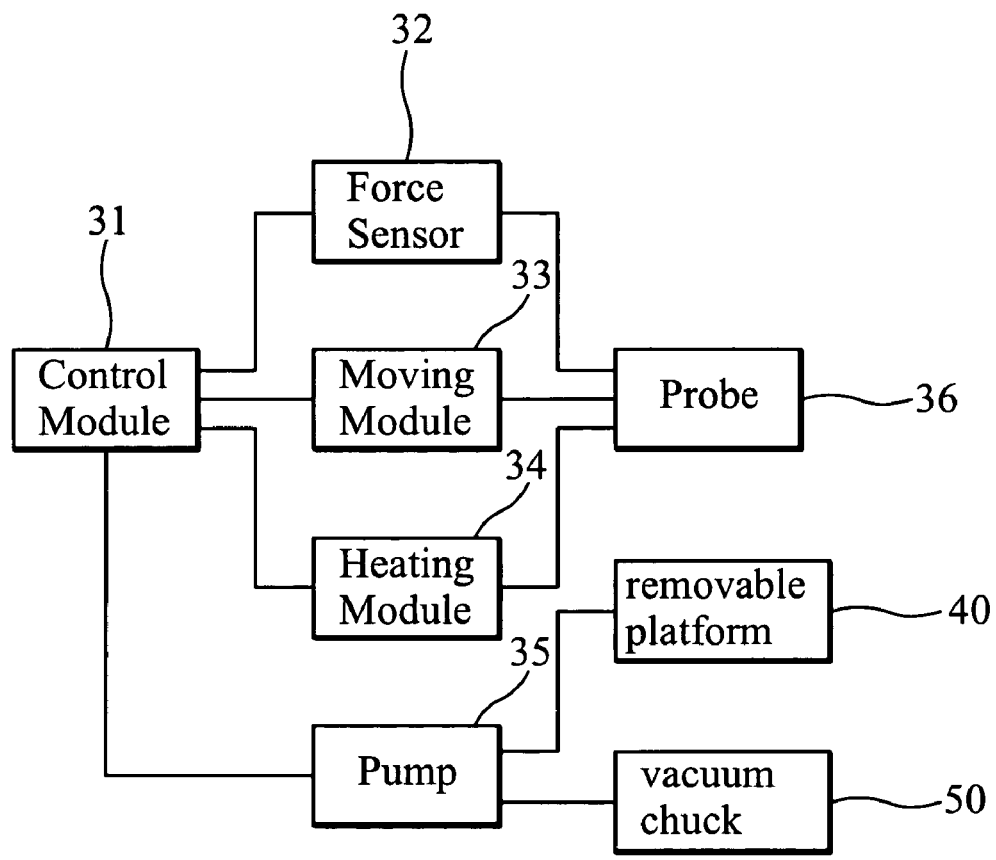
FIG. 3 is a block diagram of the shear testing apparatus of the invention.

FIG. 3 is a block diagram of the shear testing apparatus of the invention. In FIG. 3, the shear testing apparatus 30 of the invention includes a vacuum chuck 50 connected to a vacuum pump 35 to fix a large-sized wafer, a probe 36 driven by a moving module 33, and a heating module 34 for heating the probe 36 to a required temperature to proceed with the shear test. A force sensor 32 consisting of the conventional strain gauges is applied to the probe 36 to measure the pulling shear force of the contact bump formed on the wafer. A control module 31 controls the moving module 33, the heating module 34 and the vacuum pump 35 and transforms the analog signal from the force sensor 32 into digital shear force data. Furthermore, the shear testing apparatus 30 also includes a removable platform 40 which can be assembled on the vacuum chuck 50 and connected to the vacuum pump 35 to fix a small-sized wafer, such that the shear testing apparatus 30 of the invention can test two different sizes of wafers to save cost.

Figure 4:
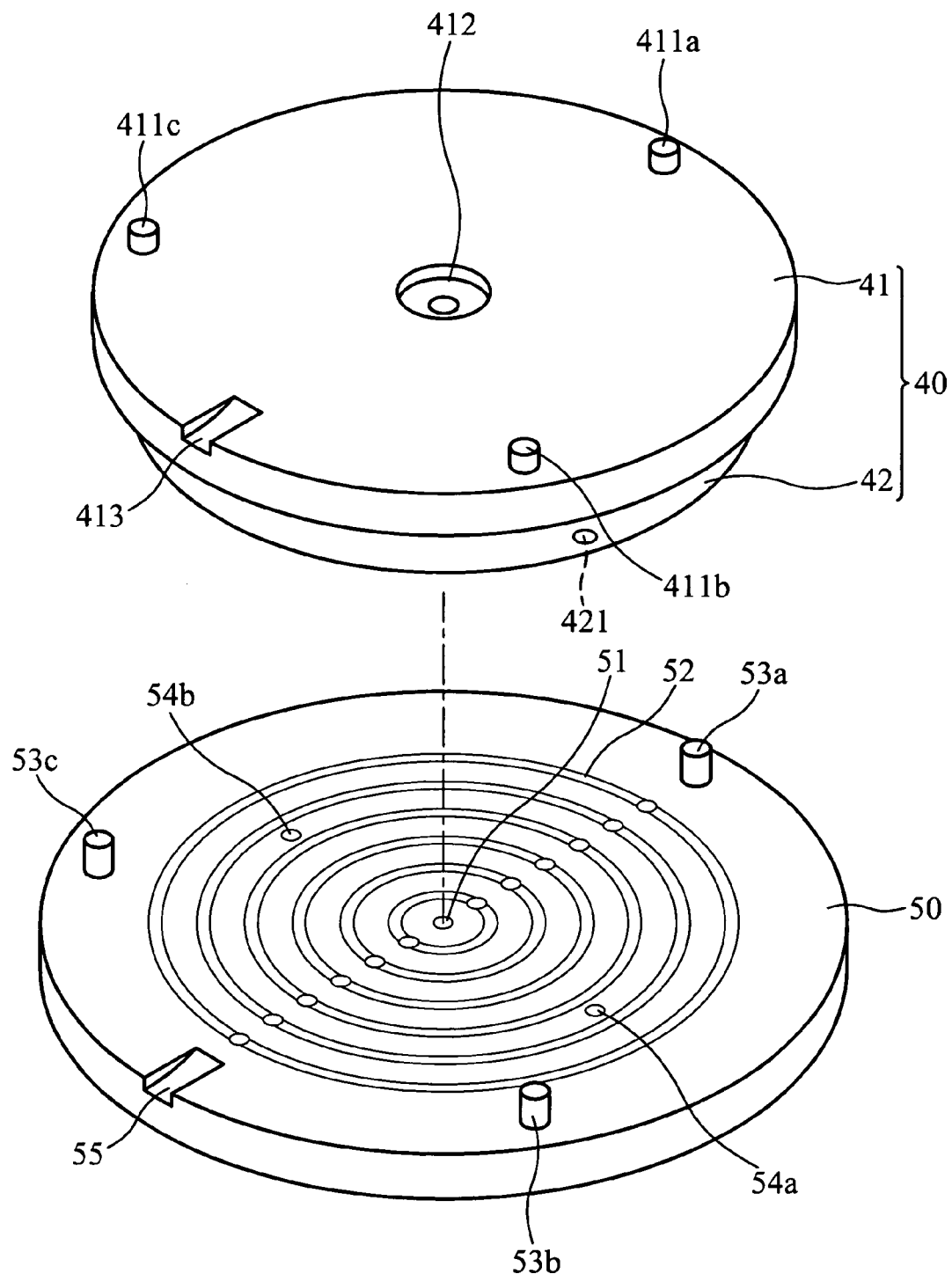
FIG. 4 is an exploded view of the vacuum chuck and the removable platform of the invention.

FIG. 4 shows the vacuum chuck and the removable platform of the invention. In FIG. 4, the vacuum chuck 50 is used to support a large-sized wafer, such as a 12" wafer, or the removable platform 40. The vacuum chuck 50 has a plurality of pins 53a~53c on the top surface to position the large-sized wafer and the removable platform 40 and two aligning holes 54a, 54b to lock the removable platform 40. The vacuum chuck 50 has a plurality of annularly arranged recesses 52, which are communicated to the vacuum pump via the linearly arranged gas-exhausting holes 51, forming a vacuum therein to fix a large-sized wafer or the removable platform 40. The vacuum chuck 50 further has a notch 55 for breaking the vacuum with a chisel when a wafer has finished the shear test.

The removable platform 40 includes a base part 42 and a moving part 41 pivotally connected thereon. The moving part 41 has a central recess 412 and a central hole 413. The base part 42 has two aligning pins (not shown), which can be inserted in the aligning holes 54a, 54b to position the removable platform 40 on the vacuum chuck 50. After the removable platform 40 is positioned on the vacuum chuck 50, 10 the central recess 412 and the central hole 413 are communicated with the vacuum pump through the annularly arranged recesses 512 and the central gas-exhausting hole 51 of the vacuum chuck 50, forming a vacuum therein to fix a small-sized wafer, such as a 6" or 8" wafer. The removable is platform 40 also has a plurality of pins 411a~411c on the top surface to position the small-sized wafer and a notch 413 for breaking the vacuum with a chisel.

Figure 5A:
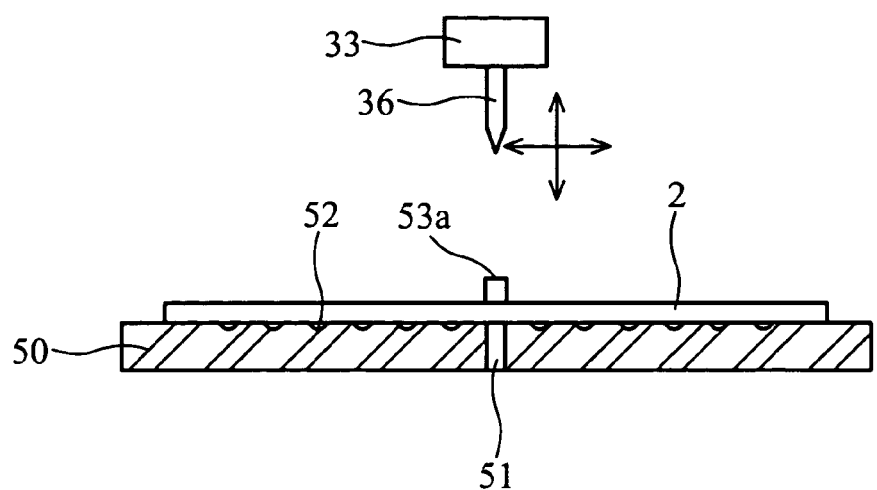
FIG. 5A is a cross section showing a 12" wafer positioned on the vacuum chuck for further shear test.
Figure 5B:
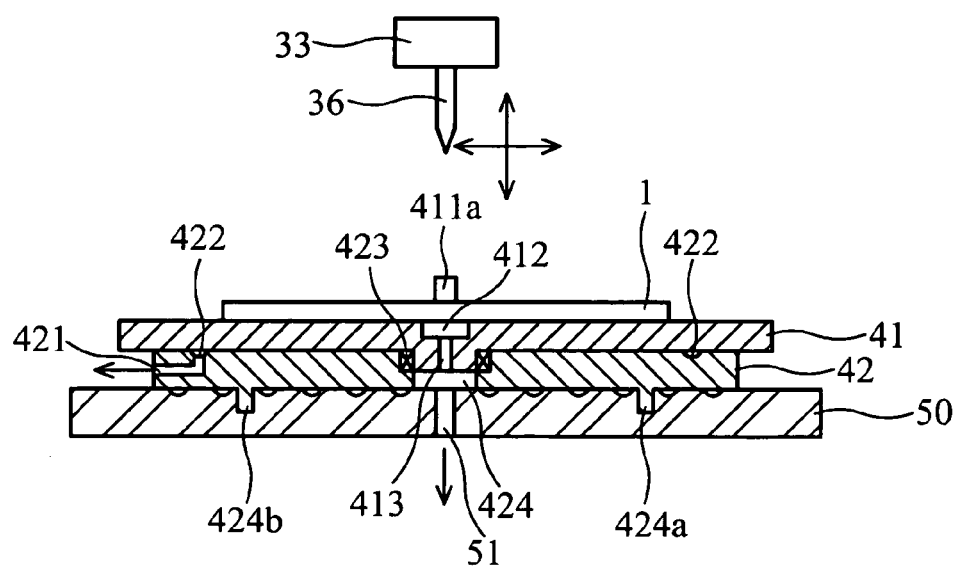
FIG. 5B is a cross section showing a 8" wafer positioned on the removable platform for further shear test.

FIG. 5A shows a 12" wafer 2 positioned on the vacuum chuck 50 by the pins 53a~53c thereon for the shear test. In FIG. 5A, the 12" wafer 2 is adhered to the vacuum chuck 50 after the pump exhausts the air in the annular recesses 52 and the gas exhausting holes 51. The moving module 33, controlled by the control module, then shifts the probe 36 to a preset start point and proceeds with the shear test. Otherwise, when proceeding with the shear test on a small-sized wafer 1, the removable platform 40 is assembled on the vacuum chuck 50 with the aligning pins 424a, 424b inserted into the aligning holes 54a, 54b of the vacuum chuck 50 first, as shown in FIG. 5B. The moving part 41 of the removable platform 40 is pivotally connected to the base part 42 through a bearing 423, such that the small-sized wafer 2 can be further rotated on the removable platform 40. The base part 42 has a passage 421 and an annular recess 422, which are communicated to the vacuum pump through a removable pipe (not shown). After the small-sized wafer 2 is fixed on the removable platform 40, the moving part 41 can also be locked by vacuum achieved by the vacuum pump. Then, the moving module 33 shifts the probe 36 to a preset start point and proceeds with the shear test.

Figure 6:
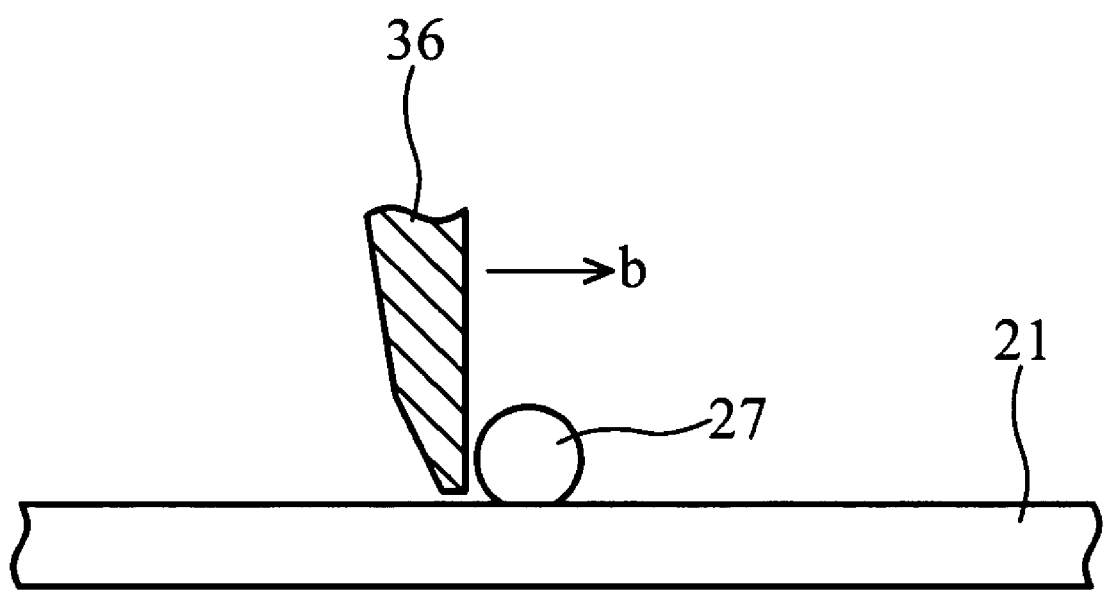
FIG. 6 is a schematic view showing the probe of the invention processing the shear test on a solder ball of a silicon substrate.

FIG. 6 shows the probe 36 of the invention processing the shear test on a solder ball 27 of a silicon substrate 21. In FIG. 6, the control module controls the moving is mechanism to shift a probe 36 to a start point contacting or almost contacting the solder ball 27 which is located on a large-sized wafer on the vacuum chuck or a small-sized wafer on the removable platform when the removable platform is disposed on the vacuum chuck. The moving mechanism moves the probe 36 in a direction (b) to separate the solder ball 27 from the wafer 21. The force sensor with strain gauges applied on the probe 36 measures the pulling force exerted on the probe 36 when the probe 36 is moved in the direction to separate the solder ball 27 from the wafer 21. Finally, the control module transforms the analog signal from the force sensor into a digital shear force data which can be displayed on a monitor.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An apparatus for testing the junction strength of a solder ball formed on an electrode of a first-sized substrate or a second-sized substrate, comprising:
    a removable platform, securing the first-sized substrate;
    a vacuum chuck, securing one of the second-sized substrate or the removable platform;
    a moving module;
    a probe, fixed on the moving module;
    a control module, controlling the moving module to shift the probe to contact the solder ball and move the probe in a direction to separate the solder ball from the second-sized substrate secured on the vacuum chuck or the solder ball from the first-sized substrate on the removable platform when the removable platform is fixed on the vacuum chuck; and
    a sensor, measuring the pulling force exerted on the probe when the probe is moved in a direction and separates the solder ball from the first-sized substrate or the second-sized substrate.

2. The apparatus as claimed in claim 1, further comprising:
    heating means for heating the probe.

3. The apparatus as claimed in claim 1, wherein the vacuum chuck has a plurality of aligning holes, and the removable platform has a plurality of aligning pins which are inserted in the aligning holes to position the removable platform on the vacuum chuck.

4. The apparatus as claimed in claim 1, wherein the removable platform has a plurality of first pins to position the first-sized substrate.

5. The apparatus as claimed in claim 1, wherein the vacuum chuck has a plurality of second pins to position the second-sized substrate or the removable platform.

6. The apparatus as claimed in claim 1, further comprising a vacuum pump.

7. The apparatus as claimed in claim 6, wherein the vacuum chuck has a plurality of annularly arranged recesses and gas-exhausting holes communicated with the vacuum pump, wherein the vacuum pump forms a vacuum therein to secure the second-sized substrate or the removable platform.

8. The apparatus as claimed in claim 7, wherein the moving part has a central recess and a central hole, and when the removable platform is positioned on the vacuum chuck, the central recess and the central hole are communicated with the vacuum pump through the annularly arranged recesses and the gas-exhausting holes of the vacuum chuck, wherein the vacuum pump forms a vacuum therein to secure the first-sized substrate.

9. The apparatus as claimed in claim 6, wherein the removable platform includes a base part and a moving part pivotally connected thereon.

10. The apparatus as claimed in claim 6, wherein the base part of the removable platform has a locking recess and a passage communicated with the vacuum pump to fix the position of the moving part.

11. An apparatus for testing the junction strength of a solder ball formed on an electrode of an 8" wafer or a 12" wafer, comprising:
    a removable platform, securing the 8" wafer;
    a vacuum chuck, securing a 12" wafer or the removable platform;
    a moving module;
    a probe, fixed on the moving module;
    a control module, controlling the moving module to shift the probe to contact the solder ball and move the probe in a direction to separate the solder ball from the second-sized substrate secured on the vacuum chuck or the solder ball from the 8" wafer on the removable platform when the removable platform is fixed on the vacuum chuck; and
    a sensor, measuring the pulling force exerted on the probe when the probe is moved in a direction and separates the solder ball from the 12" wafer or the 8" wafer.

12. The apparatus as claimed in claim 11, further comprising:
    heating means for heating the probe.

13. The apparatus as claimed in claim 11, wherein the vacuum chuck has a plurality of aligning holes, and the removable platform has a plurality of aligning pins which are inserted in the aligning holes to position the removable platform on the vacuum chuck.

14. The apparatus as claimed in claim 11, wherein the removable platform has a plurality of first pins to position the 8" wafer.

15. The apparatus as claimed in claim 11, wherein the vacuum chuck has a plurality of second pins to position the 12" wafer or the removable platform.

16. The apparatus as claimed in claim 11, further comprising a vacuum pump.

17. The apparatus as claimed in claim 16, wherein the vacuum chuck has a plurality of annularly arranged recesses and gas-exhausting holes communicated with the vacuum pump, wherein the vacuum pump forms a vacuum therein to secure the 12" wafer or the removable platform.

18. The apparatus as claimed in claim 16, wherein the removable platform includes a base part and a moving part pivoted thereon.

19. The apparatus as claimed in claim 17, wherein the moving part has a central recess and a central hole, and when the removable platform is positioned on the vacuum chuck, the central recess and the central hole are communicated with the vacuum pump through the annularly arranged recesses and the gas-exhausting holes of the vacuum chuck, wherein the vacuum pump forms a vacuum therein to secure the 8" wafer.

20. The apparatus as claimed in claim 16, wherein the base part of the removable platform has a locking recess and a passage communicated with the vacuum pump to fix the position of the moving part.

* * * * *